(12) United States Patent
Lewis

(10) Patent No.: US 10,092,470 B2
(45) Date of Patent: *Oct. 9, 2018

(54) PATIENT LIFTER WITH INTRAOPERATIVE CONTROLLED TEMPERATURE AIR DELIVERY SYSTEM

(71) Applicant: Randall J. Lewis, Bethesda, MD (US)

(72) Inventor: Randall J. Lewis, Bethesda, MD (US)

(*) Notice: Subject to any disclaimer, the term of this patent is extended or adjusted under 35 U.S.C. 154(b) by 369 days.

This patent is subject to a terminal disclaimer.

(21) Appl. No.: 13/999,369

(22) Filed: Feb. 18, 2014

(65) Prior Publication Data

US 2015/0231009 A1     Aug. 20, 2015
US 2017/0239116 A9     Aug. 24, 2017

Related U.S. Application Data

(63) Continuation-in-part of application No. 13/373,557, filed on Nov. 18, 2011, which is a
(Continued)

(51) Int. Cl.
*A61G 7/10*       (2006.01)
*A61F 7/00*       (2006.01)
*A61G 7/057*     (2006.01)

(52) U.S. Cl.
CPC .............. *A61G 7/1021* (2013.01); *A61F 7/00* (2013.01); *A61G 7/1028* (2013.01);
(Continued)

(58) Field of Classification Search
CPC ..... A47C 21/04; A47C 21/042; A47C 21/044; A47C 21/048; A47C 27/082; A47C 27/10;
(Continued)

(56) References Cited

U.S. PATENT DOCUMENTS 3,449,776 A    6/1969   Brock ............................... 5/627
3,644,950 A    2/1972   Lindsay et al. ................... 5/709
(Continued)

FOREIGN PATENT DOCUMENTS

JP     2002/000669     1/2002     ............. A47C 17/04

OTHER PUBLICATIONS

AirMatt-Patent Transfer System, http://www.medicalsearch.com.au/Products/_-_Patient_Transfer-20804.
(Continued)

*Primary Examiner* — Nicholas F Polito
(74) *Attorney, Agent, or Firm* — Ernest A. Buff & Associates, LLC; Ernest D. Buff; Margaret A. LaCroix

(57) ABSTRACT

A combination patient-transfer and intraoperative heater device has a top and bottom chamber separated by a barrier. The patient rests on the top chamber, which has a plurality of apertures for discharge of temperature-controlled filtered heated or cooled air at a regulated pressure for patient comfort and mitigation of infection. Heated or cooled filtered air is delivered to the area surrounding the patient, maintaining body temperature during anaesthesia. The bottom chamber has a plurality of apertures. When air pressure is low or off, the bottom chamber is flat and un-inflated. When air pressure is increased, air enters the bottom chamber and the apertures emit air, creating an air cushion facilitating lateral movement of the lifter device. The device performs two functions that now require separate devices and air blowers, it saves space and reduces both costs and complexity in the operating room while mitigating risk of infection.

12 Claims, 11 Drawing Sheets

Related U.S. Application Data continuation-in-part of application No. 12/150,730, filed on Apr. 30, 2008, now Pat. No. 8,555,440.

(52) U.S. Cl.
CPC . *A61F 2007/006* (2013.01); *A61F 2007/0091* (2013.01); *A61G 7/05784* (2016.11)

(58) Field of Classification Search
CPC .............. A61G 7/05761; A61G 7/1025; A61G 7/1026; A61G 7/1028; A61G 2007/05784; A61G 2007/05792; A61G 7/1021; A61F 7/0097; A61F 7/0053; A61F 7/00; A61F 2007/0288; A61F 2007/0091; A61F 2007/006

See application file for complete search history.

(56) References Cited

U.S. PATENT DOCUMENTS

| | | | | |
|---|---|---|---|---|
| 3,667,073 | A | 6/1972 | Renfroe | 5/81.1 R |
| 3,740,777 | A | 6/1973 | Dee | 5/714 |
| 3,757,366 | A | 9/1973 | Sacher | 5/423 |
| 3,778,851 | A | 12/1973 | Howorth | 5/423 |
| 3,822,425 | A | 7/1974 | Scales | 5/710 |
| 4,279,044 | A | 7/1981 | Douglas | 5/714 |
| 4,391,009 | A * | 7/1983 | Schild | A61G 7/05776 297/180.11 |
| 4,944,060 | A | 7/1990 | Peery et al. | 5/713 |
| 5,022,110 | A | 7/1991 | Stroh | 5/710 |
| 5,065,464 | A * | 11/1991 | Blanchard | A61G 7/103 180/125 |
| 5,109,560 | A | 5/1992 | Uetake | 5/713 |
| 5,113,539 | A | 5/1992 | Strell | 5/710 |
| 5,168,589 | A | 12/1992 | Stroh et al. | 5/710 |
| 5,249,318 | A | 10/1993 | Loadsman | 5/710 |
| 5,416,935 | A | 5/1995 | Nich | 5/423 |
| 5,483,709 | A | 1/1996 | Foster et al. | 5/81.1 R |
| 5,522,871 | A * | 6/1996 | Sternlicht | A47C 21/048 128/849 |
| 5,561,873 | A | 10/1996 | Weedling | 5/713 |
| 5,590,428 | A | 1/1997 | Roter | 5/726 |
| 5,652,987 | A | 8/1997 | Fujita | 5/726 |
| 5,781,943 | A | 7/1998 | Moenning et al. | 5/81.1 C |
| 6,065,166 | A | 5/2000 | Sharrock | 5/630 |
| 6,073,291 | A * | 6/2000 | Davis | A61B 6/0485 414/676 |
| 6,336,237 | B1 * | 1/2002 | Schmid | A47C 21/044 5/423 |
| 6,546,576 | B1 * | 4/2003 | Lin | A47C 21/044 5/423 |
| 7,090,692 | B1 | 8/2006 | Augustine et al. | 607/107 |
| 7,114,204 | B2 | 10/2006 | Patrick | 5/81.1 R |
| 7,278,179 | B2 | 10/2007 | Schneider | 5/714 |
| 7,565,709 | B2 | 7/2009 | Davis | 5/710 |
| 7,627,910 | B2 | 12/2009 | Davis | 5/81.1 R |
| 7,735,164 | B1 | 6/2010 | Patrick | 5/81.1 HS |
| 7,914,611 | B2 | 3/2011 | Vrzalik et al. | 96/11 |
| 2003/0084510 | A1 | 5/2003 | Lin | 5/423 |
| 2004/0237203 | A1 * | 12/2004 | Romano | A47C 27/122 5/713 |
| 2007/0136952 | A1 | 6/2007 | Sargent | 5/726 |
| 2007/0261548 | A1 * | 11/2007 | Vrzalik | A47C 21/044 95/52 |
| 2008/0000030 | A1 | 1/2008 | Wang | 5/713 |
| 2009/0320211 | A1 | 12/2009 | Lau | 5/713 |
| 2010/0024123 | A1 | 2/2010 | Davis | 5/81.1 R |
| 2012/0079656 | A1 * | 4/2012 | Lewis | A61F 7/00 5/81.1 R |
| 2012/0144584 | A1 | 6/2012 | Vrzalik | 5/600 |
| 2015/0096120 | A1 * | 4/2015 | Scarleski | A47C 31/105 5/484 |

OTHER PUBLICATIONS

AirPal-Patient Air Lift, http://www.kcil.com/asp.
Hover Tech International—HoverMatt, http://hovermatt.com/media_pdf/HoverMatt_Brochure.pdf.

\* cited by examiner

[Prior Art]

[Prior Art]

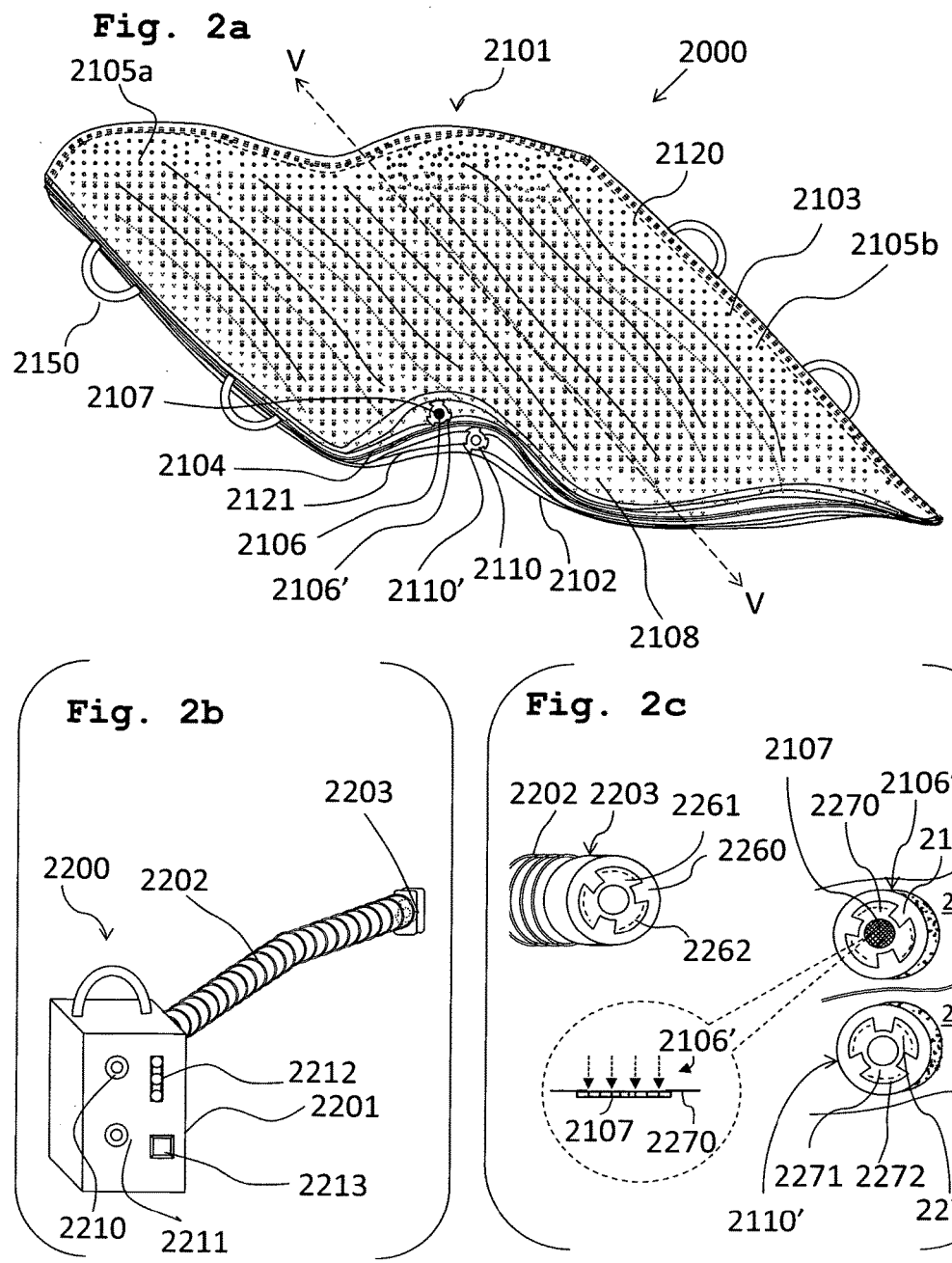

PATIENT LIFTER WITH INTRAOPERATIVE CONTROLLED TEMPERATURE AIR DELIVERY SYSTEM

This application is a continuation-in-part of U.S. Ser. No. 12/373,557 filed Nov. 18, 2011, entitled Patient Lifter With Intraoperative Controlled Temperature Air Delivery System, which in turn is a continuation-in-part of U.S. Pat. No. 8,555,440, filed Apr. 30, 2008, entitled Patient Lifter With Intraoperative Controlled Temperature Air Delivery System, the disclosures of which are hereby incorporated in their entirety by reference thereto.

BACKGROUND OF THE INVENTION

1. Field of the Invention

The present invention relates to a patient transfer system, and more particularly to a patient lifter device that also emits heated or cooled air that surrounds a patient resting thereon, maintaining desired body temperature during surgery.

2. Description of the Prior Art

The lateral transfer of patients, especially in the operating room, can be a difficult and poorly controlled procedure. Not only can the patient be injured during the process, but lateral patient transfer often contributes to back injuries incurred by hospital personnel, the most common work-related injury to hospital workers. The development of an air lifter, similar to a hovercraft, represents a significant advance in handling of patients. Making the device disposable has obvious advantages for sterility and cleanup. However, there is resistance in employing such disposable devices for single usage because of associated costs. As a result, use of disposable lateral transfer devices is generally limited to special situations, such as transporting very large patients.

Disposable intraoperative heaters are already in general use, generally employing a simple heated air blower and a light plastic "tent". Thermal coverings have been provided. The most common alternatives are water mats, filled with heated circulating water. While effective, these mats often come apart during patient transfer, causing a veritable flood on the operating room floor, and necessitating significant cleanup.

Examples of various patient support systems and/or transporters are set forth below.

U.S. Pat. No. 3,449,776 to Brock discloses a collapsible telescoping stretcher including a plurality of flexible straps attached to the stretcher adapted to tie down the legs and torso of the patient to the stretcher. An inflatable mattress rests on the stretcher and has separate leg portions whereby the straps can be used to tie down the legs individually. A collapsible telescoping head support is mounted on the stretcher and had adjustable torso members. Straps extend through the head support and torso members for immobilizing a broken neck. The stretcher does not provide a patient lifter having heated/cooled air released from a top chamber. Further, there is no discharge of air on the bottom surface of the stretcher enabling the creation of an air cushion that facilitates the lateral movement of a patient.

U.S. Pat. No. 3,644,950 to Lindsay et al. discloses a patient support system. Included with the system is a bed for supporting and treating a hospital patient. A lamination of low and medium density plastic foam is enclosed in a pressurized container. An open pore foam layer on top of the container produces a flow of air from the top of the foam layer for patient ventilation. Control of the volume of air varies the degree of ventilation. The pressurizing air for the container is controlled to vary the relative firmness of support. The patient support of the '950 patent provides ventilation around the patient delivered through foams of different density. The ventilation air is not heated. There is no discharge of air on the bottom surface of the patent support system enabling the creation of an air cushion that facilitates the lateral movement of a patient.

U.S. Pat. No. 3,667,073 to Renfroe discloses a patient transporter. This apparatus provides for effortless moving of a non-ambulatory patient from a bed or operating table to a cart, e.g., recovery room stretcher or the like and from the cart to other non-porous surfaces, e.g., X-ray tables, etc. The patient transporter discharges compressed air through the apertures in the bottom of an inflatable mattress to levitate the mattress from an impervious stretcher or bed during lateral transport of the patient. The compressed air may be discharged from apertures provided on top of the inflatable mattress to essentially levitate the patient with burns or severe injury by a plurality of air jets. The efficacy of this system is questionable. Strong air jets may even aggravate the patient's skin injury. While the discharge of compressed air at the bottom of the inflatable mattress facilitates the lateral movement of the patient, the patient transporter does not provide heated air surrounding the patient.

U.S. Pat. No. 3,740,777 to Dee discloses a bed support. This bed support holds all or part of the human body and includes a chamber having an upper wall at least part of which is of thin flexible sheet material, e.g. rubber film, adapted when supported by gas pressure in the chamber to define a trough in which the item may lie. The body support device merely inflates balloons surrounding an individual body portion and the balloons have apertures that discharge air towards the body part through PTFE or polyethylene disks. This discharge of air through the apertures and the disk separates the balloons' external surfaces from the body part by the flow of air. No air is discharged on the bottom of the body support, with the result that a patient laying on the body support cannot be easily transported laterally. Moreover, no heated air is discharged to surround the patient and thereby provide warmth and comfort.

U.S. Pat. No. 3,757,366 to Sacher discloses a cushion for preventing and alleviating bedsores. The cushion for preventing and alleviating bedsores includes a warm air delivery system which delivers warm air in the close area of the cushion that contacts the skin of the patient, thereby preventing direct contact between the skin and the cushion and preventing or alleviating bedsores. No air is discharged below the cushion since the bottom portion of the cushion is indicated to be non-porous. Thus, the cushion with the patient laying there above may not be easily transported laterally.

U.S. Pat. No. 3,778,851 to Howorth discloses a mattress for use in treating a patient who has undergone extensive surgery or who has been severely burned. The mattress comprises an upper panel, a lower panel, and means for supplying air to the space between the two panels. The lower panel is made of air-impermeable material. At least a part of the upper panel is perforated to allow conditioned air to issue forth and pass around the patient. Since the lower portion of the mattress is indicated to be impermeable, no air is delivered in the bottom of the mattress. As a result, a patient lying on the mattress may not be easily transported laterally.

U.S. Pat. No. 3,822,425 to Scales discloses an inflatable support appliance. The inflatable support apparatus of the '425 patent has an air impermeable base with air impermeable protrusions to which an air permeable cap is mounted. A person supported by these caps receives air through the apertures provided in the cap, preventing direct contact between the person and the cap. No air is delivered at the bottom, since the base and the protrusions are air impermeable. As a result, when a patient is supported by the caps, the lateral movement of the patient is very difficult, if not impractical.

U.S. Pat. No. 4,279,044 to Douglas discloses a fluid support system for a medical patient. No air is delivered around the patient and no air is released on the bottom of the support system. The lateral movement of the patient from a stretcher to an operating system is not facilitated.

U.S. Pat. No. 4,391,009 to Schild et al. discloses a ventilated body support. This ventilated support for living bodies comprises an inflatable alternating pressure pad, which is either enclosed by or forms a part of an air permeable plenum chamber through which air is pumped at low pressure to provide a source of ventilating air to a body resting on the support. The alternating pressure pad which is inflated by a high pressure pump has two sets of interdigitized cells which are alternately inflatable and deflatable and carry the weight of a body alternately, on each of the two sets of cells. The disclosed ventilated body support has a plurality support tubes comprising a high pressure central sealed portion and a low pressure surrounding portion each pressurized by two tubes with individual valves from a pump. The two portions may bleed air to the environment to adjust the support character of the ventilated body support. Heated air is not released to surround the patient. No air is released in the bottom of the ventilated body support and a patient lying on the ventilated body support may not be easily transported laterally.

U.S. Pat. No. 5,022,110 to Stroh discloses a low air loss mattress. The low air loss mattress is made of multiple cushions, which are connected together and form an integral mattress which may be used on a standard hospital bed. The multiple cushions allow for variable pressure to support a patient and to compensate for different weights of various portions of the body of the patient. Each cushion is provided with air vents in its upper surface to provide air circulation around a patient and for pressure regulation in each cushion. The air may be heated. Retainers are provided to prevent billowing of each cushion in its center portions and maintain a substantially level patient support surface. A small portable blower provides a constant air supply for each of the cushions and allows adjustment of the air pressure in each of the cushions to accommodate varying weights of patients on the mattress. Any release of air occurs only on the patient contacting surface, and the air may be heated. There is no discharge of air on the bottom of the low air loss mattress, which does not function as a transfer device.

U.S. Pat. No. 5,109,560 to Uetake discloses a ventilated air mattress with alternately inflatable air cells having communicating upper and lower air chambers. The ventilated air mattress with alternately inflatable air cells has a plurality of adjacent cells. One of the cells is inflated while the adjacent cell is deflated altering the support characteristic of the air mattress at a specific body contacting location so that no individual part of the body has to support the bodyweight over a period of time. The deflating of the cell is accomplished by opening a valve and the air is not heated and is not discharged surrounding the patient. No air is discharged from the bottom surface of the ventilated air mattress and therefore, moving a patient lying on the air mattress laterally is not assisted by an air cushion.

U.S. Pat. No. 5,113,539 to Strell discloses a body supporting device such as a mattress, box spring, cushion or car seat having an inner coil spring structure. The device is provided with adjustable firmness by means of a plurality of inflatable pneumatic members. The pneumatic members are positioned within the interstices formed between adjacent coil springs in a variety of patterns. The pneumatic members are connected to an inflation control device for adjusting the firmness of the body supporting device in varying modes, including a pulsation mode to provide a messaging affect. No air is discharged from the top or bottom surface of the body supporting device. Moving a patient lying on the air mattress laterally is not assisted by an air cushion and no temperature control is achieved.

U.S. Pat. No. 5,168,589 to Stroh et al. discloses a pressure reduction air mattress and overlay. This patent is a continuation in part of U.S. Pat. No. 5,022,110, discussed above. Multiple cushions allow for variable pressure to support a patient and to compensate for different weights of various portions of the body of the patient. Each cushion is provided with air vents in its upper surface to provide air circulation around a patient and for pressure regulation in each cushion. The air may be heated. Retainers are provided to prevent billowing of each cushion in its center portions and maintain a substantially level patient support surface. A small portable blower provides a constant air supply for each of the cushions and allows adjustment of the air pressure in each of the cushions to accommodate varying weights of patients on the mattress. Any release of air occurs only on the patient contacting surface and the air may be heated. There is no discharge of air on the bottom of the low air loss mattress and it is not a transfer device. There is no air cushion under the mattress assisting this movement.

U.S. Pat. No. 5,249,318 to Loadsman discloses an air cushion support. This air inflatable support appliance has internally sealed seams, internal diaphragms and internal structural support members. The air cushion support of the '318 invention provides a flow of air between the top portion of the support and the patient lying there over requiring no cover or draw sheet. There is no discharge of air on the bottom of the air cushion support, and this device does not aid in the lateral transfer of the patient between a stretcher and an operating table.

U.S. Pat. No. 5,416,935 to Nieh discloses a surface air conditioning device including a plurality of passages through a support surface which overlies a closed volume in which temperature conditioned air is supplied; each passage is provided with a pressure actuated flow control valve which is normally closed to prevent loss of conditioned air through the associated passage; pressure contact with the valve effects opening thereof to allow conditioned air to flow through the passage. The top chamber includes partitions, barriers or coil springs located therein. Thus, the surface air conditioning device is not readily compressed to a substantially flat structure under the patient when not in use and as compressed the surface air conditioning device would be lumpy under the patient, causing discomfort. Moreover, the coiled spring obstructions require the volume of the chamber to be increased to accommodate the springs, and in turn, increased pressure is needed to achieve optimum air delivery to the patient.

U.S. Pat. No. 5,483,709 to Foster et al. discloses a low air loss mattress with rigid internal bladder and lower air pallet. It is not disposable, and is primarily thick mattress. This mattress has an upper patient supporting low air loss bladder for ventilating and preventing skin degeneration of a patient supported. It does not have any temperature control feature. Unlike the submitted device, it has an intermediate rigidly inflatable static bladder which must become relatively rigid upon inflation to aid in transferring or weighing a patient. A lower high air loss bladder is provided for reducing the friction force between the mattress and the supporting surface to facilitate surface-to-surface transfers. The high air loss bladder includes a peripheral tube, which seals against a supporting surface to contain the air, which escapes from longitudinal sacks within the tube. The foot sections of the low air loss and static bladders are selectively deflatable. The low air loss mattress has a low air loss bladder 12, an intermediate rigidly inflatable static bladder 14 and a lower high air loss bladder 18. The low air discharge bladder releases air surrounding the patient, reducing patient contact with the low air loss bladder. The air volume is generally small due to the small space separation between the patient and the top portion of the device. An intermediate pressurized rigid bladder supports the patient. The lower high air loss bladder serves to create an air cushion that allows the patient on the device to be moved easily. The low air loss bladder locally 'floats' the patient off the mattress surface. Moreover, the low air discharge air bladder does not provide heated air and does not have sufficient air delivery capacity to surround the area around the patient with warm air.

U.S. Pat. No. 5,561,873 to Weedling discloses an air chamber-type patient mover air pallet with multiple control features. The air chamber-type patient mover air pallet does not have separate upper and lower chambers disconnected from each other, the first chamber providing controlled heated or cooled air surrounding the patient for temperature control while a second separated chamber having adequate air flow provides an air cushion for easy transverse movement of a patient.

U.S. Pat. No. 5,590,428 to Roter discloses an air pressurized person supporting device with ventilation. The upper wall is formed with a plurality of openings at spaced locations receiving a plurality of valve members. Valves in the supporting device seal off everywhere except where the person applies pressure, providing ventilation of air. Since no air is released under the support device, there is no air cushion, and the device does not function to lift or transport. Further, the device does not provide heated air surrounding the patient.

U.S. Pat. No. 5,652,987 to Fujita discloses a decubitus ulcer prevention device. This decubitus ulcer prevention device comprises an air generator with a fan and an air mattress for receiving air from the air generator. Air is discharged at a surface through minute air discharge holes. Along a flow path of the air that passes through the fan are located, in order as named, a heater and an alkaline chlorine dioxide gas generator, in which is internally provided a ceramic body that is impregnated with an alkaline chlorine dioxide solution. Air that is heated, by passing through the heater, is brought into contact with the ceramic body, so that air that includes alkaline chlorine dioxide gas is thus supplied to the air mattress. The decubitus ulcer prevention device delivers heated air or ambient air treated with chlorine dioxide through fine apertures on the skin contacting surface of an air mattress. This complex system is not a transfer device; air is not delivered on the underside of the air mattress and the air mattress with the supported patient may not be easily displaced in a transverse direction. The device is not designed to be disposable.

U.S. Pat. No. 5,781,943 to Moenning et al. discloses a medical table and method for moving a patient from a first position to a second position. This medical table includes a base. The medical table with roller support uses a motor to rotate the rollers to change the position of the patient. No air is delivered on the bottom surface of the medical table. The lateral movement of the patient is not accomplished by the movement of an air mattress. Instead, the patient is driven by rollers and a belt under the patient, and has to be assisted by medical personnel for proper placement. Once the patient leaves this medical table, the patient has to be moved manually, causing hardship to the patient.

U.S. Pat. No. 6,073,291 to Davis discloses an improved inflatable medical patient transfer apparatus having a combination of transverse partition members and a raised perimeter section that reduces deleterious ballooning and uneven inflation as well as quick emergency deflation and provides additional security for a patient supported upon such transfer apparatus. Additional differentially inflatable patient rolling chambers are preferably supplied on the top of the transfer apparatus to provide assistance to medical personnel in beginning to roll patients reclining or lying upon the transfer apparatus, particularly in a deflated condition on a hospital bed. An improved air inlet arrangement is also provided along with certain indicia upon the surface of the transfer apparatus to expedite use by hospital personnel. The inflatable apparatus includes a top chamber having a raised peripheral chamber containing partition members, and the inside of the chamber includes partition members. As a result, the surface is not flat and the inner partition members result in a device that is cumbersome and bulky when compressed, causing discomfort to the patient. The raised peripheral chamber and partition members result in greater volume in the chamber, in turn causing greater air flow to be needed.

U.S. Pat. No. 6,065,166 to Sharrock discloses a support cushion for a person in a lateral decubitus position, comprising a base, two lateral structural supports, and a central concavity. The lateral supports are sufficiently stiff to resist rolling of the person, while the central concavity distributes the weight of the person. The device is a holder—a support cushion designed to hold the patient still while the patient is on the operating table. It is not designed for or applicable to patient transfer, and does not involve a heating or temperature control element.

U.S. Pat. No. 6,546,576 to Lin discloses structure of a ventilated mattress with cooling and warming effect. This structure of a ventilated mattress with cooling and warming effect comprises a mattress body, a warming/cooling air-delivery controlling box, and a connecting tube. The control box produces warming/cooling air to the mattress body via the connecting tube and the warming/cooling air is released via a plurality of ventilation buttons mounted at the surface of the mattress body. Thereby, the mattress provides the user with a warming/cooling effect. The mattress is not an air mattress, but has conventional springs to support a patient positioned on the mattress. No air is delivered at the bottom surface of the mattress. Due to the absence of an air cushion at the bottom surface of the mattress, a patient lying on the mattress may not be laterally moved with ease.

U.S. Pat. No. 7,090,692 to Augustine et al. discloses a thermal blanket. The blanket lies above the patient, rather than below. This thermal blanket includes an inflatable covering with a head end, a foot end, two edges and an undersurface. The covering is inflated through an inlet at the foot end by a thermally-controlled inflating medium. An aperture array on the undersurface of the covering exhausts the thermally-controlled inflating medium from the covering. When inflated, the thermal blanket self-erects and provides a bath of thermally-controlled inflating medium to the interior of the erected structure. The blanket has an aperture free top surface and a side facing the patient is provided with a plurality of apertures to discharge warm air that is supplied to the blanket. Furthermore, nothing in the device facilitates lateral movement of the patient; it is not a transfer device.

U.S. Pat. No. 7,114,204 to Patrick discloses a method and apparatus for transferring patients. This patient transfer apparatus includes an inflatable mattress, alternatively having a rigid top board with a patient restraint system on which a patient can be placed, when patient immobilization is required. A portable cart is included with a chamber for storage of a plurality of mattresses. The cart also has a gas/air blower and power supply system for empowering the blower. Pressurized air is supplied to a single chamber of an air mattress, which discharges the air through the underside of the mattress, and not independently into an upper or lower chamber. While this passage of air creates an air cushion under the mattress, permitting lateral displacement of the patient, there is no indication that the pressure of supplied air is regulated. No warm air is delivered to the patient positioned on the upper surface of the mattress device, and patient temperature is not controlled.

U.S. Pat. No. 7,627,910 to Davis discloses a transfer mattress including an upper mattress having three longitudinally oriented plenums and three separate inlet/outlet valves that are each arranged in airflow communication with their respective plenum. First and second of the plenums are arranged in airflow communication with one another while a central plenum is arranged in airflow isolation from the first plenum and the second plenum so that the first and second plenums may be inflated and deflated independently of the central plenum. A lower inflatable mattress is separated by a common wall from the upper mattress. A lower inlet/outlet valve is arranged in airflow communication with a lower plenum defined by the lower inflatable mattress. A bottom wall defines a plurality of perforations so that when the lower plenum is charged with pressurized air, it escapes under pressure through the perforations to create an air bearing under the mattress. A method for transporting a patient in comfort is also provided by the invention. The inflatable apparatus includes a top chamber having raised peripheral chamber containing partition members, and the inside of the chamber includes partition members. As a result, the surface is not flat and the inner partition members result in a device that is cumbersome and bulky when compressed, causing discomfort to the patient. The raised peripheral chamber and partition members result in greater volume in the chamber, in turn causing greater air flow to be needed.

U.S. Pat. No. 7,278,179 to Schneider describes an inflatable mat with vent structures controlled by heat sensors. It is used to treat skin breakdown. It is not a transfer device and no air is expelled from the lower surface. Heat serves only to change the chemical structure of the upper surface to allow air to circulate to the skin. The device is not used in an operating room or designed to maintain body temperature.

U.S. Pat. No. 7,565,709 to Davis discloses a double chambered transfer mattress capable of partial deflation, and which includes a top inflatable mattress and a bottom inflatable mattress that are separated by a common wall from one another. A selectable inlet/outlet valve is arranged for airflow communication between an interior chamber of the bottom inflatable mattress and a source of pressurized air. A one-way valve is positioned through the common wall so as to provide selective air flow communication between the top inflatable mattress and the bottom inflatable mattress. When the inlet/outlet valve is closed, air continues to escape from perforations in the bottom inflatable mattress, and the one-way valve is actuated so as to prevent deflation of the top inflatable mattress. The inflatable apparatus includes a top chamber having raised peripheral chamber containing partition members, and the inside of the chamber includes partition members. As a result, the surface is not flat and the inner partition members result in a device that is cumbersome and bulky when compressed, causing discomfort to the patient. The raised peripheral chamber and partition members result in greater volume in the chamber, in turn causing greater air flow to be needed.

U.S. Pat. No. 7,735,164 to Patrick discloses a disposable patient transfer mattress including a rectangular top sheet, a rectangular bottom sheet, internal baffles, and a receptacle configured to receive a connector for supplying air to inflate the mattress. The bottom sheet corresponds to the top sheet, and the periphery of the bottom sheet is joined to the periphery of the top sheet. The internal baffles extend between the top sheet and the bottom sheet. Each baffle is a rectangular sheet with first and second parallel edges, and each baffle is joined to the top sheet along the first edge and to the bottom sheet along the second edge. The bottom sheet has a plurality of holes configured to provide a continuous cushion of air under the mattress when the mattress is inflated. The top sheet, bottom sheet, and internal baffles are made of fabric backed with a thermally weldable material, where the thermally weldable material faces the interior of the mattress for facilitating thermal welding of the baffles to the top surface and the bottom surface. Pressurized air is supplied to a single chamber of an air mattress, which discharges the air through the underside of the mattress, and not independently into an upper or lower chamber. While this passage of air creates an air cushion under the mattress, permitting lateral displacement of the patient, there is no indication that the pressure of supplied air is regulated. No warm air is delivered to the patient positioned on the upper surface of the mattress device, and patient temperature is not controlled.

U.S. Pat. No. 7,914,611 to Vrzalik discloses a support system including a multi-layer cover sheet with a number of layers. In certain embodiments, a source to move air inside and outside the multi-layer cover sheet can be provided. The source can include a source of positive pressure or negative pressure. The mattress is not a transfer device, does not have air vents below or above, and has no temperature regulating action.

U.S. Pub. Pat. App. No. 2008/0000030 to Wang discloses an inflatable mattress designed for more than one body to be supported on its surface. The mattress is not a transfer device, does not have air vents below or above, and has no temperature regulating action.

U.S. Pub. Pat. App. No. 2009/0320211 to Lau discloses an inflatable bed assembly having a plurality of inflatable cushion cells disposed on the top of the inflatable bed. Each cushion cell has a vent fluidly interconnecting the interior volume of the cushion cell with a main air chamber of the bed. When the bed is inflated, the cushion cells inflate and form raised projections on the top of the bed. The cushion cells provide a pressure sensitive surface which molds to the user's body for increased comfort. The vents are sized to allow the cushion cells to inflate upon inflation of the main air chamber, partially deflate when pressure is applied, and re-inflate when the pressure is removed. The size of the vents dampens the rate that air passes through the vent. The controlled inflation and deflation of the cells softens the impact caused by application of a body thereon and simulates the dampened response of "memory-foam". The mattress is not a transfer device, does not have air vents below or above, and has no temperature regulating action.

Foreign Patent Publication No. JP2002000669 to Masato et al. discloses a bed and chair for nursing and care. The bed or chair is lifted upwards by pumping air into an air pad. No air is delivered at the bottom of a mattress to create an air cushion that facilitates movement of a patient. This '669 merely raises a bed or a chair.

"AirMatt—Patent Transfer System" at web location http://www.midmed.com.au/index.php?module=pagesetter&func=viewpub&tid=2&pid=55& header=1 discloses Airmatt|Lateral Air Transfer System. The AirMatt system only provides air at the bottom surface of the mattress for easy displacement of a patient. No heated air is delivered from the top surface of the mattress for temperature control during surgery and the mattress is not disposable.

"AirPal—Patient Air Lift" at web location http://www.airpal.com/manual1.pdf discloses a patient transfer system. The AirPal—Patient Air Lift has a mattress on which the patient is positioned. Air is supplied to the mattress to enable the lateral movement of the patient, who floats on an air cushion. The mattress is not moved. Rather, the floating patient is moved. No warm air surrounds the patient.

"Hover Tech International—HoverMatt" is found at web location http://www.hovermatt.com/. The brochure is available at http://www.hovermatt.com/media_pdf/HoverMatt_Brochure.pdf. It discloses the HoverMatt® Air Transfer Mattress. The HoverMatt provides air directly under the patient forming an air cushion so that the patient can be laterally slid on the mat. There is no air provided on the bottom surface of the mat forming an air cushion. The mat is not laterally slid. Instead, the patient is slid by an attendant. No warm air surrounds the patient.

None of the devices described hereinabove teaches or discloses a dual function patient lifter with temperature control. temperature control devices described are associated with heavy mattresses. The thick supporting structures are designed for longer term or continuous usage, and not for the short term, transient application of patient transfer. Further, none of the devices provides an inter-operative pad that delivers filtered clean air to surround the patient. Most of the devices are not practical for single usage and disposal.

SUMMARY OF THE INVENTION

The present invention provides a system and method to lift and laterally transfer a patient that also delivers temperature-controlled air intraoperatively from below the patient, maintaining body temperature during surgery. The lifter/transfer portion of the device (bottom chamber) is only inflated briefly to achieve transfer of the patient and is otherwise collapsed; it is not a static mattress. The ambient air bottom chamber of the patient lifter is inflatable for use to transfer the patient to a different support structure, such as a mattress, stretcher, or other surface.

It has been surprisingly and unexpectedly found that a single pad can be constructed to deliver clean filtered warm air from below a patient without the need of a tent structure; yet, at the same time, be appointed to deliver ambient air to a bottom chamber for easy movement of the pad when transferring the patient. None of the currently disclosed or utilized devices provides an intra-operative heater providing clean filtered air around a patient that incorporates a lifter/transfer mechanism that moves a patient on and off the operating table without excessive force and effort, avoiding pain for the patient and possible injury to operating room personnel. It has also been found that lateral transfer conducted with minimal tilt of the patient, reducing rolling and pulling, reduces the risk of disruption of operative repair and dislocation of prosthesis.

Moreover, most current devices that provide warm air delivery do so by means of a tent apparatus that blows air up over a patient. These tent devices are large and bulky and when inflated sometimes interfere with access to the patient. The use of the tents can be avoided by using the subject patient lifter/heater, where apertures on the top surface of the top chamber deliver warm/cooled air effectively from below the patient. A blanket or surgical drape that is normally placed over the patient and pad entraps the warm/cooled air. Other current devices that attempt to provide warmth from below the patient are typically water blankets that heat below a patient. These water blankets frequently rupture and flood the operating table and floor. The need for water blankets also can be avoided with use of the patient lifter/heater. It has been found that the air surrounding the patient is susceptible to carrying airborne bacteria. As a result, it has been determined that the bacteria in the air can cause infection.

It has been surprisingly and unexpectedly found that the usefulness of the lifter is significantly improved by combining it with an intraoperative heater. The intraoperative heater is also improved when it is combined with a patient lifter/transfer device. The use of a single device saves time, space, and cost and avoids the possible transfer of bacteria, fluids or organic material from one patient to another via a non-disposable (i.e., re-used) pad. The air flowing in and out of the upper chamber is regulated according to pressure and temperature, and it is generally delivered at low pressure. Moreover, the air in the upper chamber is preferably filtered to prevent bacteria from being blown in the air circulating around the patient and help maintain sterility and avoid infection. A more powerful blower is then provided to push the air through a bacterial filter in the upper chamber. The "ambient" air provided to the lower chamber does not need to be filtered, as it doesn't circulate around the patient during the surgical procedure and it is normally supplied at high pressure to create the air cushion during transfer.

The system of the present invention comprises a combination heater and transfer device, consisting of a mat with a bottom surface and a top surface, a heated air top compartment, and an ambient air bottom chamber separated by a diaphragm. The top surface has a plurality of apertures. The heated air top chamber has an inlet aperture attached to a hose. Heated air travels through the heated air chamber. Apertures on the top surface of the pad deliver heated air from below a patient resting on the top surface of the pad. A surgical drape above the patient contains that warm air and maintains body temperature without the need of a cumbersome tent or water blanket. The lifter/transfer portion of the device (bottom chamber) is only inflated briefly to achieve transfer of the patient and is otherwise collapsed. It is not a static mattress. The device's ambient air bottom chamber is inflated for use when a patient requires transfer to a different support structure, such as a stretcher or hospital bed. The ambient air bottom chamber is constructed with small holes in the bottom surface to allow air to exit, creating an air cushion that slightly levitates the pad above the underlying surface. This facilitates transfer of the patient from the stretcher to an operating table. When the patient needs to be moved laterally, the air pressure in the bottom chamber is increased to a level whereby air leaks from the apertures in the bottom surface of the device. An air cushion is thereby created, substantially decreasing the friction for lateral displacement of the device on which the patient rests, so that even a heavy patient may be moved with minimal effort by a single person. Advantageously, with this arrangement hospital personnel are spared the difficult work of lifting and sliding the patient, and the frequent back strains that result from this activity.

Advantageously, the lifter/heater device performs all of its functions using a single blower/motor with variable (high/low) air output and a heater that is switched on or off. High pressure/volume air flow without heat in the lower chamber is used for the transfer function and low pressure with heated (or potentially cooled) air in the upper chamber maintains correct patient temperature. The dual functions of the air blower save space in the operating room or other location and reduce cost because only one machine is needed for two different functions.

In operation, the patient rests on the device, which has been placed on a bed or stretcher. When the patient is to be transferred to another support structure, operating table or the like, pressure-regulated compressed air is delivered to the bottom chamber of the pad. The air escapes from apertures provided on the bottom surface, allowing the pad and the patient to be lifted and transferred easily onto a separate structure.

In a further embodiment of the invention, the lower chamber of the pad includes at least two inter-digitizing inflatable chambers that extend along the length of the pad. Ambient air is delivered into the bottom compartment and the two inter-digitizing inflatable chambers. These inter-digitizing inflatable chambers allow the device to serve as an alternating pressure pad. Each of the two individual inter-digitizing inflatable chambers is pressurized alternately by the regulated air pressure which can be channeled by a valve into one of the two chambers. Air pressure within these sections is alternately increased and decreased, changing the points of contact between the patient's skin and the top surface of the pad and thereby reliving pressure on sores or skin injury locations.

BRIEF DESCRIPTION OF DRAWINGS

The invention will be more fully understood and further advantages will become apparent when reference is had to the following detailed description of the preferred embodiments and the accompanying drawings, in which:

FIG. 2a illustrates a first embodiment of the subject invention;

FIG. 2b illustrates a blower appointed to be utilized with the subject invention to provide heated/cooled air and ambient air to the top and bottom chambers, respectively;

FIG. 2c illustrates detail of the hose attachment of the blower to the top and bottom chambers;

FIG. 5b illustrates a cross-section view of the embodiment of FIG. 5a;

FIG. 6b illustrates a cross-section view of the embodiment of FIG. 6a.

DESCRIPTION OF THE PREFERRED EMBODIMENTS

Figure 1A:
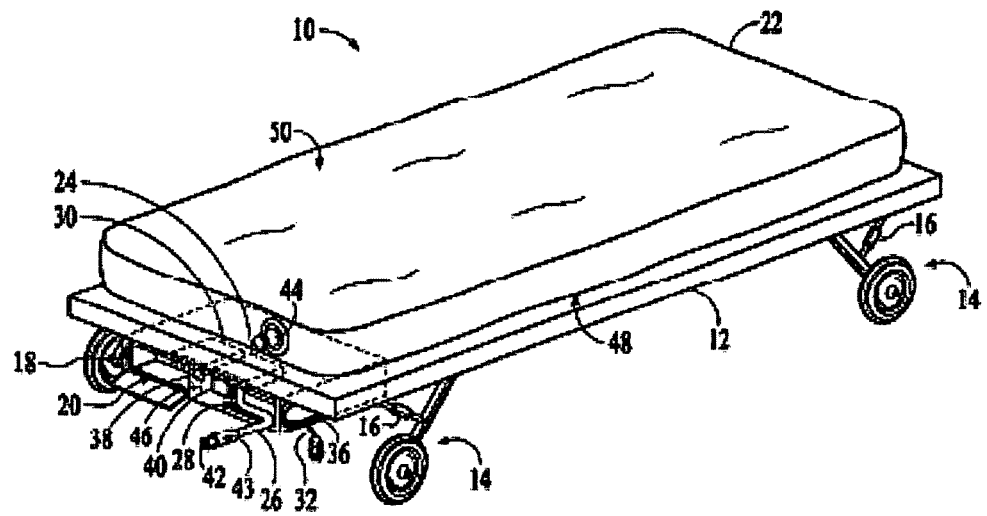
FIG. 1a illustrates an air mattress for patients of the type disclosed by the prior art.

Patients are oftentimes required to be transported from a hospital bed to an X-ray, CT or MRI facility for laboratory tests. A patient may also be required to be transported from the hospital bed or stretcher to an operating table. Patients often have painful limbs or fractures, and any movement of the patient may result in extreme discomfort. Further, patients with high body weight are generally more difficult to move, and the lateral transfer of a patient can injure the patient and cause back injuries to the hospital staff. Recent development of airlift mattresses, as for example those marketed by AirMatt, AirPal or HoverMatt have produced air mattresses with air cushion-forming apertures thereunder. These air-cushion forming apertures enable a patient positioned on the mattress to be laterally displaced on or off a flat or irregular surface with minimal effort. The patient may be laterally moved from a hospital bed to a stretcher, or from a stretcher to an x-ray table or an operating table with ease. However, these airlift mattresses do not surround the patient with controlled temperature airflow. As a result, the patient requires the use of another device to maintain body temperature during anaesthesia. Conventional methods for ambient temperature control surrounding the patient generally require use of tents that are bulky and at times awkward. Water blankets are effective, but often rupture or leak. However, it has been determined that the surrounding air can cause bacterial infections in patients.

It has been surprisingly and unexpectedly found that the usefulness of the lifter is significantly improved by combining it with an intraoperative heater. The intraoperative heater is also improved when it is combined with a patient lifter/transfer device. The use of a single device saves time, space, and cost and avoids the possible transfer of bacteria, fluids or organic material from one patient to another via a non-disposable (i.e., re-used) pad. The air flowing in and out of the upper chamber is regulated according to pressure and temperature, and it is generally delivered at low pressure. Moreover, the air in the upper chamber is preferably filtered to prevent bacteria from being blown in the air circulating around the patient and help maintain sterility and avoid infection. A more powerful blower is then provided to push the air through a bacterial filter in the upper chamber. The "ambient" air provided to the lower chamber does not need to be filtered, as it doesn't circulate around the patient during the surgical procedure and it is normally supplied at high pressure to create the air cushion during transfer.

The subject patient lifter includes an upper chamber wherein air is introduced into the patient lifter. A filter is integrated within the patient lifter to remove air-borne infectious disease. Preferably, a more powerful blower is utilized with the patient lifter because the filter would impose additional drag on the air stream. Advantageously, the filter eliminates bacteria from the heated or cooled air that is circulated around the patient. By eliminating bacteria from the air the chance of infection related to the device is significantly reduced. Placement of the filter is on the inside surface of the attachment piece for the upper chamber so that the filter is fully disposable in that location and doesn't require cleaning or periodic replacing. Further, the positioning of the filter in the upper chamber is also desirable because it functions only in a low airflow situation, making it less likely to blow out or burst when air flows through it. As the air flow in the lower compartment is not obstructed, it also reduces the power that the pump must deliver to achieve the high flow that is necessary when the patient is being lifted and transported.

Figure 1B:
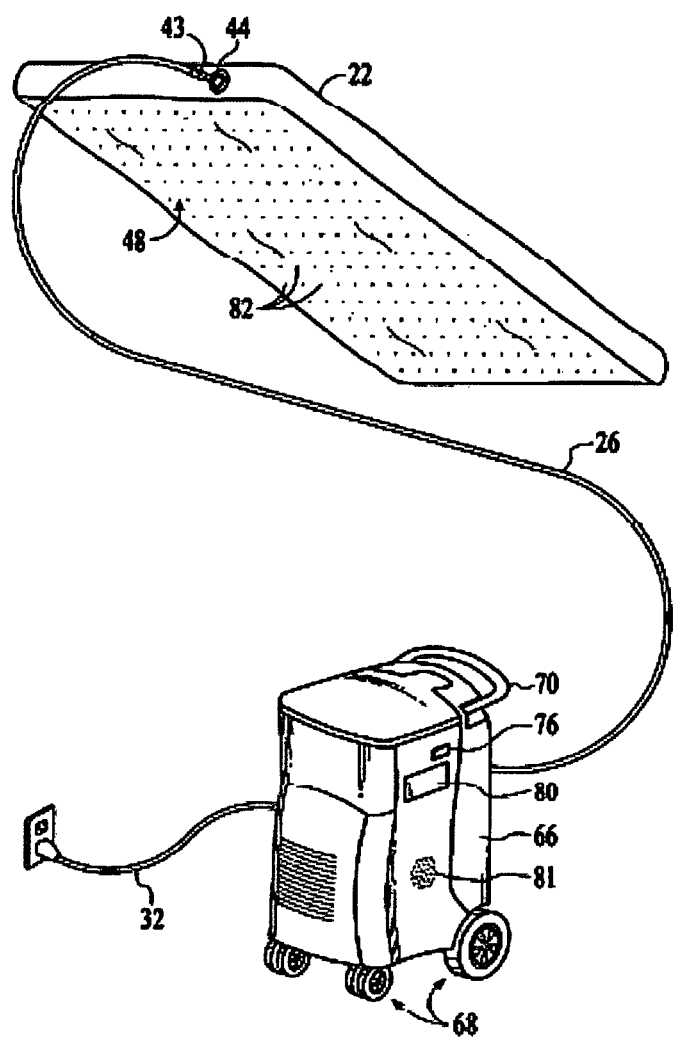
FIG. 1b illustrates an air mattress for patients of the type disclosed by the prior art.
Figure 3:
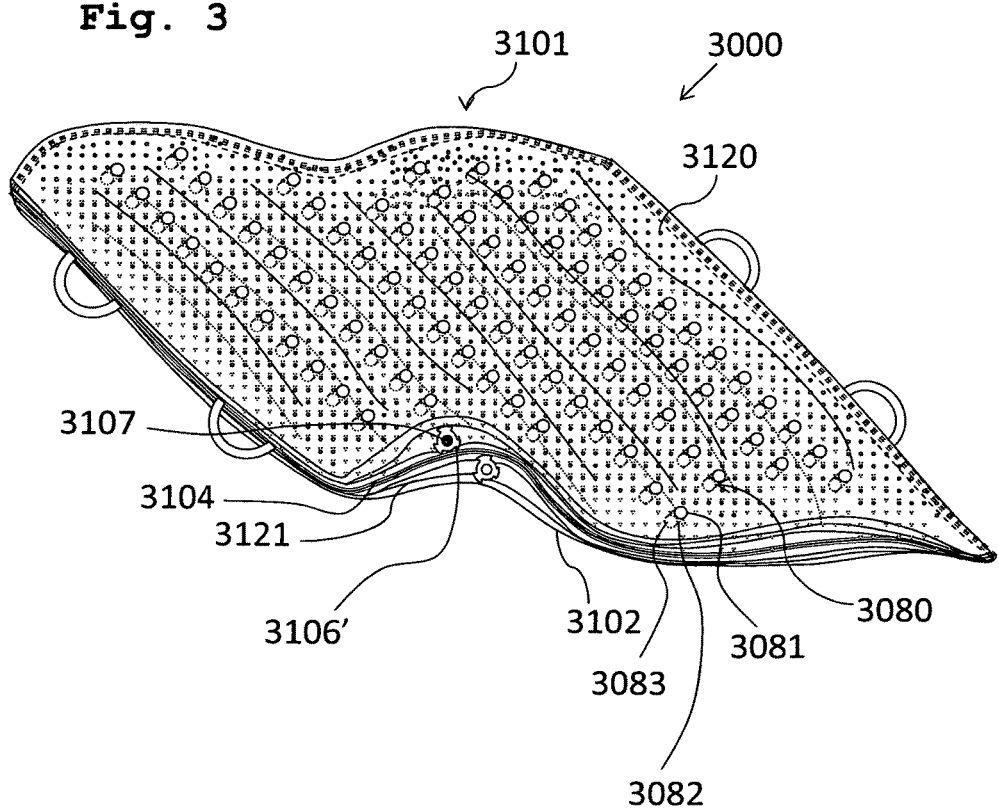
FIG. 3 illustrates another embodiment of the subject invention, wherein the pad's top and bottom chambers include perforation channels contiguously there through for fluid drainage.

FIGS. 1a and 1b depict a prior art inflatable air mattress disclosed by U.S. Pat. No. 7,114,204 to Patrick, which is laterally moved on an air jet cushion. This device is in contrast with the products marketed by AirMatt, AirPal or HoverMatt where the air jets are directly below the patient and the patient generally 'floats' on air, allowing easy displacement. FIG. 1a illustrates an integrated patient transfer system including an inflatable air mattress assembled on a stretcher 12 (FIG. 8 of the Patrick patent). The air cushion and supply cart according to Patrick is illustrated in FIG. 1b (FIG. 3 of the Patrick patent). The air mattress 22 is constructed with a plurality of small holes in the bottom surface 48 through which gas exits from inside the mattress 22, thereby creating an air cushion for levitating the air mattress.

Figure 2D:
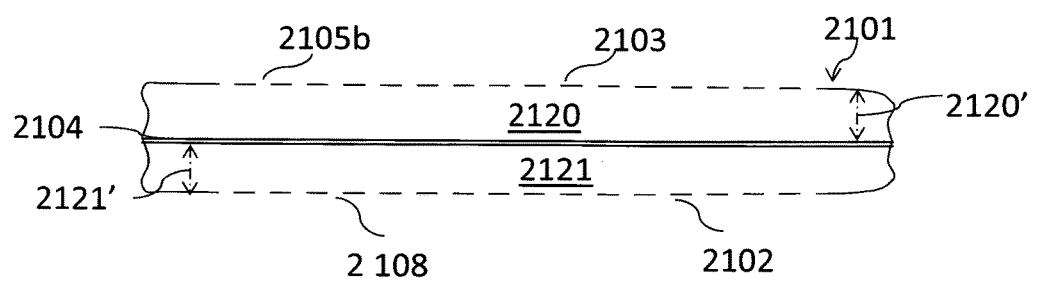
FIG. 2d illustrates a cross-section view of the embodiment of FIG. 2a taken along V-V.

FIG. 2a illustrates at 2000 a first embodiment of the subject invention. FIG. 2d illustrates a cross-section view taken along line V-V of FIG. 2a. Pad 2101 generally is a thin flexible matt construct provided with a top chamber 2120 and a bottom chamber 2121. Preferably, handles 2150 are provided at the foot and head region of the pad. Alternatively, the handles 2150 may also/or instead, be located on the sides of the pad. Pad 2101 includes a bottom surface 2102, a top surface 2103, and a separation barrier 2104 between and completely separating the top chamber 2120 and 2121. Barrier 2104 is preferably a diaphragm composed of a semi-flexible thin impervious material, such as a polymeric or silicone film or material. Top surface 2103 is provided with apertures 2105a and 2105b therein. Generally, apertures 2105a, located near the head portion of the pad 2101, may be larger than apertures 2105b located at the foot portion of pad 2101, and deliver an increased amount of comfort air to the upper portion of the body. The apertures 2105a and 2105b may be selected to be of equal size without departing from the scope of the invention. Low pressure compressed heated or cooled air is supplied to the top chamber 2120 through a hose attached to inlet 2106 by way of mating attachment means 2106' (see FIGS. 2b, 2c and 2e for embodiments relating to the hose/mating attachment means). A filter 2107 is integrated within mating attachment means 2106' and/or within inlet 2106 so that the air inflow (low flow heated/cooled) to the top chamber 2120 is filtered to remove bacteria and contaminants that can cause infection. The filter 2107 is attached to the back (inside/interior facing) part of the mating attachment means 2106' (see FIG. 2c). Filter 2107 cleans air so that clean air without bacteria is passed through the top chamber 2120 and released around the patient, minimizing infection risk. Filtered heated or cooled air travels through the top chamber 2120 and is delivered through the apertures 2105a and 2105b, to surround and provide comfort and clean air to a patient resting on the pad. Air is supplied from below the patient to provide optimal temperature maintenance during surgery while mitigating the risk of infection.

Pad 2101 functions as an air lift pad wherein the bottom chamber 2121 is pressurized by ambient compressed air delivered at a pre-selected regulated pressure through inlet aperture 2110 through a hose attached to the inlet aperture 2110 by way of mating attachment means 2110' (see FIGS. 2b and 2c for embodiments relating to the mating attachment means).

The bottom surface of the bottom chamber is provided with a plurality of apertures 2108 through which the regulated pressure compressed air delivered through aperture 2110 may leak. When transfer or lifting of the patient is not required, air delivery to the bottom chamber is generally in a low or off position, so that the bottom chamber is essentially flat or un-inflated. When it is time to initiate lifting or transfer of the patient, air delivery to the bottom chamber is increased or turned on so that regulated pressure of compressed air is delivered into the bottom chamber and flows from the apertures 2108, functioning to create an air pocket under the bottom surface 2102 of the pad and facilitating lifting or transfer of the patient and pad onto another surface. Regulated compressed air pressure is increased to a high value, and air leaks through the apertures 2108 creating an air cushion between the bottom surface 2102 of the pad and an underlying flat or uneven surface, such as a bed, stretcher or an operating table.

This air cushion essentially levitates the pad with the patient slightly above the flat or uneven surface, whereby the patient may be laterally displaced with minimal effort. Using this procedure, the patient is easily displaced laterally with minimal effort for example, from a bed to a stretcher or a stretcher to an operating table or any combination thereof. When the patient is moved to a desired location, the compressed air pressure may be brought to substantially zero or very low so that the bottom chamber is substantially flat or un-inflated.

Preferably, both the top chamber 2120 and the bottom chamber 2121 have shallow depths 2120', 2121' as best indicated by way of FIG. 2d. The depth 2121' of the bottom chamber 2121 preferably ranges from about ½ inch to about 3 inches. Owing to the shallow depth 2121' of the bottom chamber 2121, at least two advantages have been found to result. First, less air is needed to initiate air leakage through apertures 2108 when creating the air cushion and the air cushion is created at a more rapid rate than would occur with a less shallow chamber. Second, when flat or collapsed the bottom chamber does not cause any type of discomfort to a patient resting on the pad. The shallow chamber 2121 virtually eliminates formation of excess material which could cause bunching and create an uncomfortable mass under the patient's body when the chamber is flat. Preferably, the depth 2120' of the top chamber 2120 ranges from about ½ inch to about 3 inches. Further advantages are derived from a shallow top chamber. Less air is needed to initiate and maintain the desired air flow regulation of the heated/or cooled air. The structure facilitates faster inflation and air distribution delivery to the patient.

The subject pad is light, flexible and easily stored. It is fabricated from nonwoven material and is intended to be single use disposable. This reduces the risk of infection and avoids the cost and time required for cleaning. Because the device performs two functions that presently require separate devices and air blowers, it saves space and reduces both costs and complexity in the operating room. The same heater pad can also be used after a patient leaves the operating room but still requires warming to maintain body temperature.

FIG. 2b illustrates a blower shown at 2200 that is appointed to be utilized with the pad to provide heated/cooled air and ambient air to the top and bottom chambers, respectively. Generally, blower 2200 includes a main body housing 2201 removably attached to at least one hose 2202 which in turn includes an attachment fixture 2203 that is appointed to be attached to the mating attachments 2106' and 2110' of the top and bottom chamber inlets 2106, 2110, respectively. The hose allows the blower to supply air to both the top and bottom chambers when needed (such as during heated/cooled air delivery via the top chamber, and lateral transfer via the bottom chamber). Generally, the blower 2200 includes low and high air regulator controls 2210, 2211 as well as heater/cool air controls 2212 and ambient air controls 2213. Blower 2200 may be placed on a rolling cart with storage capacity for lifter/heater pads as well. Advantageously, the blower 2200 performs two functions in a single unit device, thus saving space and reducing costs in the operating room.

Figure 2E:
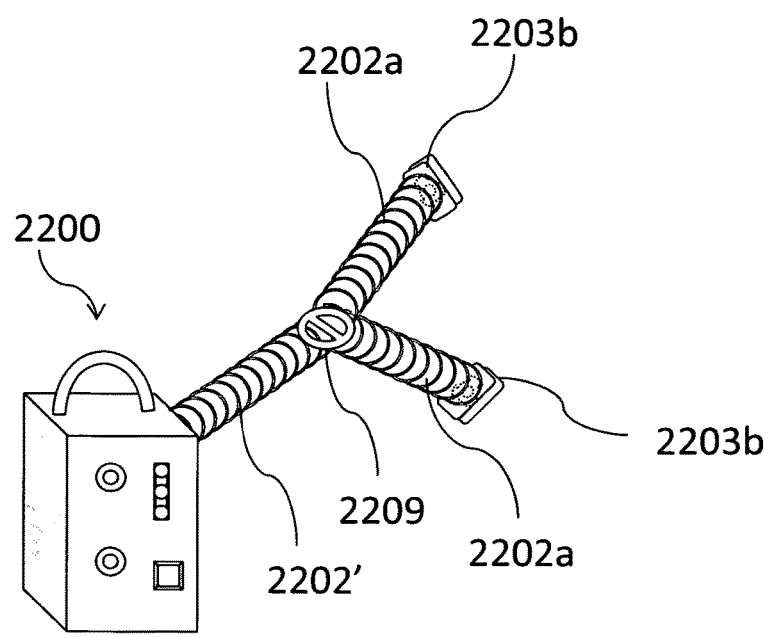
FIG. 2e illustrates a view of the blower attached to an alternate hose attachment having a diverter valve.

FIG. 2e illustrates a view of the blower attached to an alternate hose attachment having a diverter valve. Blower 2200 is attached to a hose portion 2202' that is attached to a diverter valve 2900. Diverter valve 2900 is attached to a first hose 2202a and a second hose 2202b each having attachment fixtures 2203a' and 2203b', respectively. Attachment fixtures 2203a' and 2203b' are constructed as discussed hereinabove. In this manner, the diverter valve 2900 can be adjusted to divert air either to the first or second hose 2202a, 2202b as desired.

FIG. 2c illustrates detail of the hose attachment of the blower to the top and bottom chambers. Blower 2200 attachment fixture 2203 is appointed to mating attach to mating attachments 2106' and 2110' of the top and bottom chamber's inlets 2106, 2110, respectively. Air is supplied to the top or bottom chambers through a hose that is connected with a mating attachment fitting preferably of the type shown in the FIG. 2c. Preferably, the hose 2202 terminates at the attachment fixture 2203, which is a bayonet-type fitting that engages the mating fittings 2106', 2110' of the pad. The hose is locked into position by a twisting operation. More specifically, the hose 2202 from the blower terminates in a male fitting 2261 at the end of hard plastic or rubber tube 2260. Fitting 2261 engages a complementary female fitting 2270, also made of hard plastic or rubber, integrated within mating fittings 2106', 2110' of the pad attached to the respective mattress/pad chamber. Fitting 2270 has an inward facing channel 2271 between perforated baseplate 2272 and three teeth. Male fitting 2261 also has three teeth, each with an outward facing channel 2262 that mates with fitting 2270. The thickness of the tooth portion outside the channel is tapered circumferentially, so that the fittings can be engaged and locked by inserting fitting 2261 into fitting 2271 and rotating it into locked position. Filter 2107 is integrated within mating attachment means 2106' so that the air inflow (low flow heated/cooled) to the top chamber 2120 is filtered to remove bacteria from air that surrounds the patient. The filter 2107 is attached to the back (inside/interior facing) part of the mating attachment means 2106' (see FIG. 2c). Filter 2107 cleans air so that clean air without bacteria is passed through the top chamber 2120 and released around the patient, minimizing infection risk. Filtered heated or cooled air travels through the top chamber 2120 and is delivered through the apertures 2105a and 2105b, to surround and provide comfort and clean air to a patient resting on the pad.

Air is supplied from below the patient to provide optimal temperature maintenance during surgery while mitigating the risk of infection.

FIG. 3 illustrates another embodiment of the subject invention, shown generally at 3000. Pad 3101 is generally constructed as set forth hereinabove with respect to the discussion of FIG. 2a. However, in the embodiment herein shown, pad 3101 includes perforation channels 3080 contiguously through the top chamber 3120, separation barrier 3104 and bottom chamber 3121. Perforation channels 3080 are constructed having a proximate aperture 3081, channel walls 3082, and a distal aperture 3083, each open to the atmosphere and being appointed to allow fluid drainage. A filter 3107 is integrated within mating attachment means 3106' within inlet 3106 so that the air inflow (low flow heated/cooled) to the top chamber 3120 is filtered to remove bacteria and contaminants that can cause infection. Filter 3107 cleans air so that clean air without bacteria is passed through the top chamber 3120 and released around the patient, minimizing infection risk.

Figure 4:
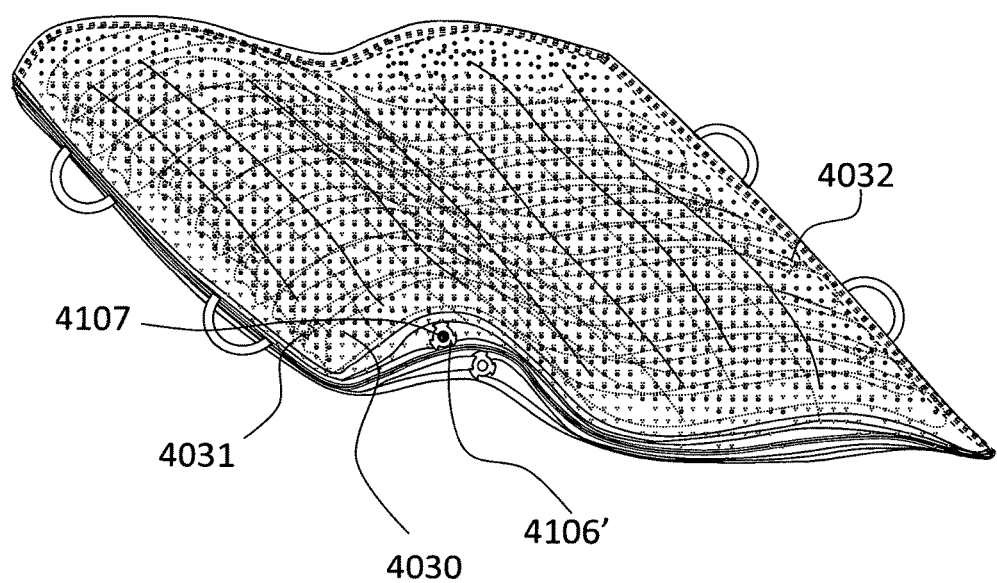
FIG. 4 illustrates another embodiment of the subject invention, wherein the top, bottom and/or both chambers are ridged and/or contain baffles to enhance dimensional stability to the device.

FIG. 4 illustrates another embodiment of the subject invention, wherein the top, bottom and/or both chambers are ridged and/or contain baffles therein 4030 to enhance dimensional stability to the device. Preferably baffles 4030 are interconnected to one another such as in an alternating manner at 4031, and/or 4032, respectively between the baffles. A filter 4107 is integrated within mating attachment means 4106' within inlet 4106 so that the air inflow (low flow heated/cooled) to the top chamber 4120 is filtered to remove bacteria and contaminants that can cause infection. Filter 4107 cleans air so that clean air without bacteria is passed through the top chamber 4120 and released around the patient, minimizing infection risk.

Figure 5A:
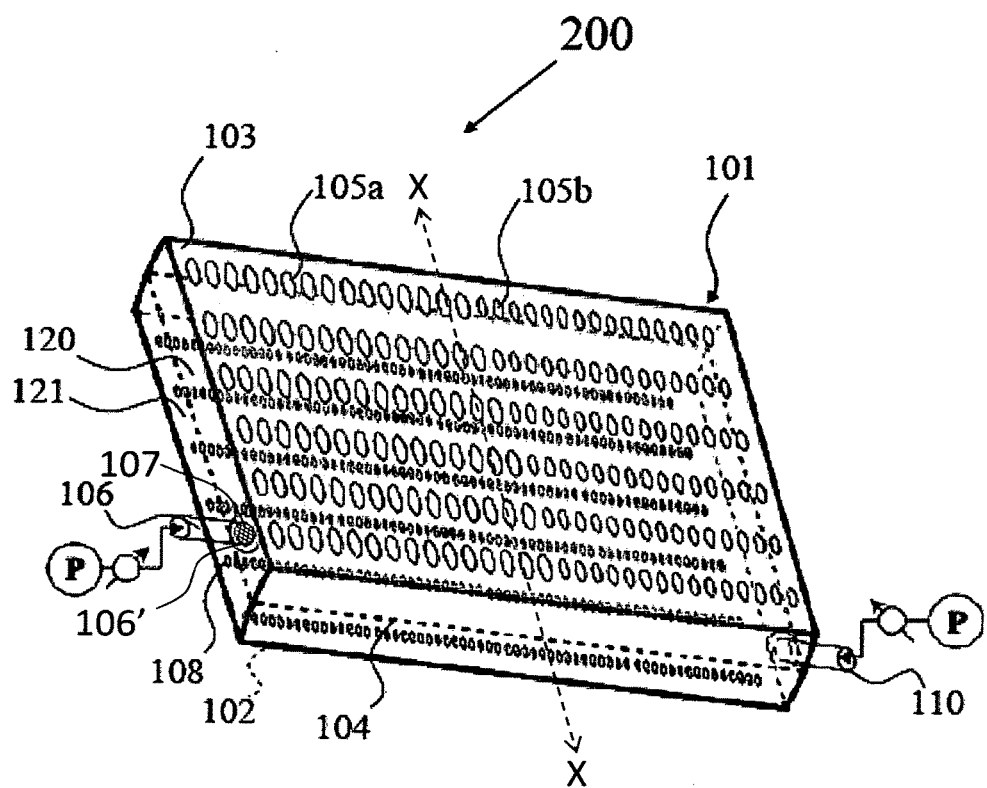
FIG. 5a illustrates a first embodiment of the subject invention.
Figure 5B:
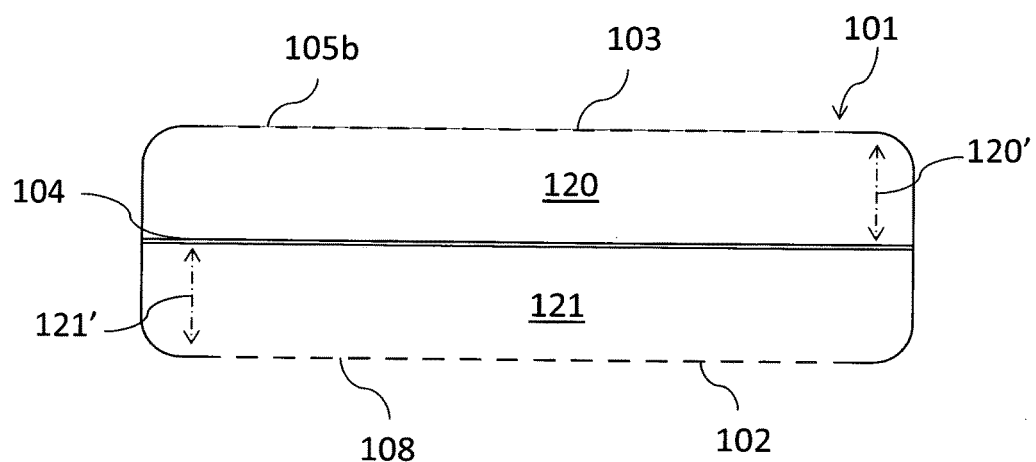

FIG. 5a illustrates at 200 a first embodiment of the subject invention. FIG. 5b illustrates a cross-section view taken along line X-X of FIG. 5a. Pad 101 generally is provided with a top chamber 120 and a bottom chamber 121. Pad 101 includes a bottom surface 102, a top surface 103, and a separation barrier 104 between the top chamber 120 and 121. Barrier 104 is preferably a diaphragm composed of a semi-flexible thin impervious material, such as a polymeric or silicone film or material. Top surface 103 is provided with apertures 105a and 105b therein. Generally, apertures 105a, located near the head portion of the pad 101, are larger than apertures 105b located at the foot portion of pad 101, and deliver an increased amount of comfort air to the upper portion of the body. The apertures 105a and 105b may be selected to be of equal size without departing from the scope of the invention. Low pressure compressed heated or cooled air is supply to the top chamber 120 through a hose attached to inlet 106. P indicates a pressure source and the circle with an arrow indicates a regulator. The heated or cooled air travels through the top chamber 120 and is delivered through the apertures 105a and 105b, to surround and provide comfort to a patient resting on the pad. Air is supplied from below the patient to provide optimal temperature control. Pad 101 functions as an air lift pad wherein the bottom chamber 121 is pressurized by ambient compressed air delivered at a pre-selected regulated pressure through aperture 110. P indicates a pressure source and the circle with an arrow indicates a regulator. The bottom surface of the bottom chamber is provided with a plurality of apertures 108 through which the regulated pressure compressed air delivered through aperture 110 may leak. A filter 107 is integrated within mating attachment means 106' within inlet 106 so that the air inflow (low flow heated/cooled) to the top chamber 3120 is filtered to remove bacteria and contaminants that can cause infection. Filter 107 cleans air so that clean air without bacteria is passed through the top chamber 120 and released around the patient, minimizing infection risk.

When transfer or lifting of the patient is not required, air delivery to the bottom chamber is generally in a low or off position, so that the bottom chamber is essentially flat or un-inflated. When it is time to initiate lifting or transfer of the patient, air delivery to the bottom chamber is increased or turned on so that regulated pressure of compressed air is delivered into the bottom chamber and flows from the apertures 108, functioning to create an air pocket under the bottom surface 102 of the pad and facilitating lifting or transfer of the patient and pad onto another surface. Regulated compressed air pressure is increased to a high value, air leaks through the apertures 108 creating an air cushion between the bottom surface 102 of the pad and an underlying flat or uneven surface, such as a bed, stretcher or an operating table. This air cushion essentially levitates the pad with the patient slightly above the flat or uneven surface, whereby the patient may be laterally displaced with minimal effort. Using this procedure, the patient is easily displaced laterally with minimal effort for example, from a bed to a stretcher or a stretcher to an operating table or any combination thereof. When the patient is moved to a desired location, the compressed air pressure may be brought to substantially zero or very low so that the bottom chamber is substantially flat or un-inflated. Preferably, both the top chamber 120 and the bottom chamber 121 have shallow depths 120', 121'. The depth 121' of the bottom chamber 121 preferably ranges from about ½ inch to about 3 inches. Owing to the shallow depth 121' of the bottom chamber 121, two advantages result. First, less air is needed to initiate air leakage through apertures 108 when creating the air cushion and the air cushion is created at a more rapid rate than would occur with a less shallow chamber. Second, when flat or collapsed the bottom chamber does not cause any type of discomfort to a patient resting on the pad. The shallow chamber 121 virtually eliminates formation of excess material which could cause bunching and create an uncomfortable mass under the patient's body when the chamber is flat. Preferably, the depth 120' of the top chamber 120 ranges from about ½ inch to about 3 inches. Further advantages are derived from a shallow top chamber. Less air is needed to initiate and maintain the desired air flow regulation of the heated/or cooled air. The structure facilitates faster inflation and air distribution delivery to the patient.

Figure 6A:
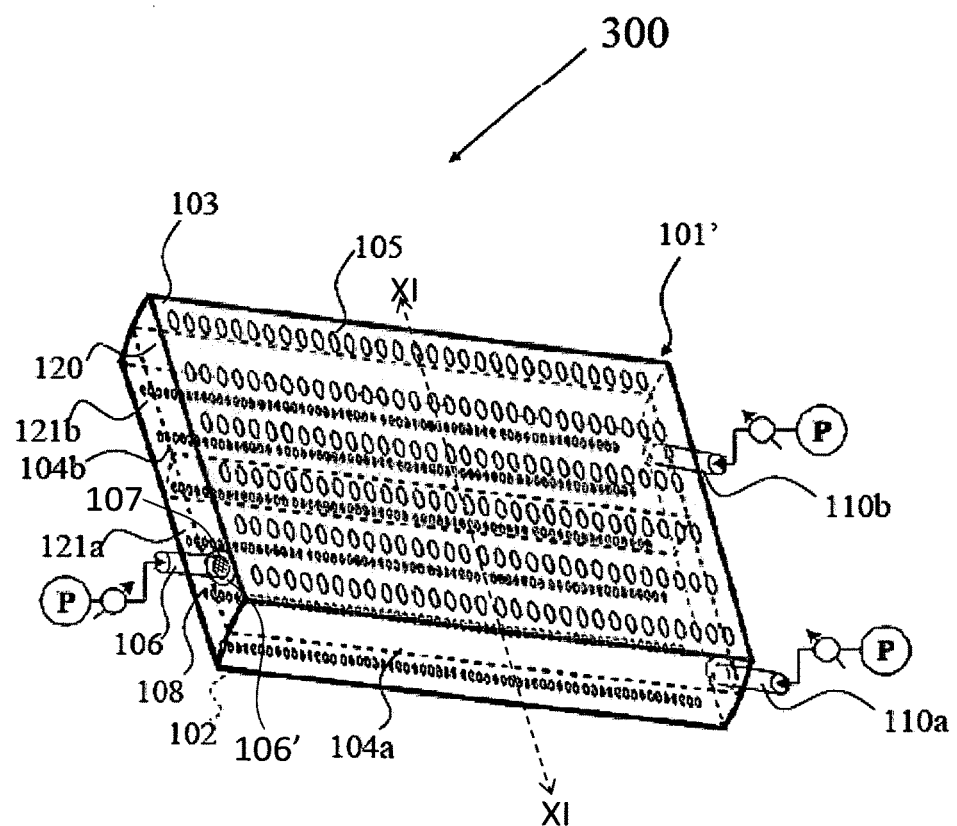
FIG. 6a illustrates an alternative embodiment of the subject invention.
Figure 6B:
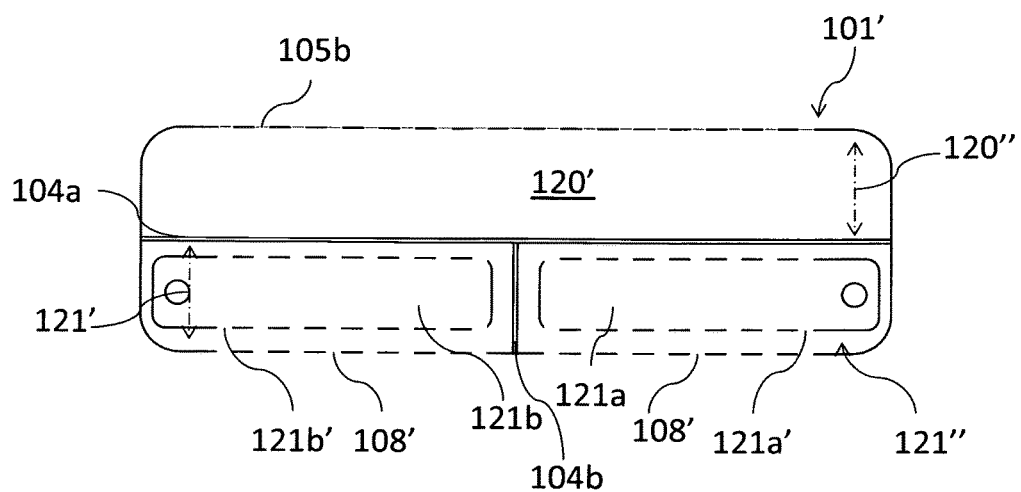

FIG. 6a illustrates at 300 the second embodiment of the subject invention. FIG. 6b illustrates a cross-sectional view taken along XI-XI of the embodiment of FIG. 6a. The intraoperative controlled temperature device can be used for heating and/cooling of the immediate area surrounding the patient, by providing the circulation of heated air or cooled air using a low pressure blower. Similar numerical indicia as FIGS. 5a-5b are used for clarity. Pad 101' is provided with a top chamber 120" and a bottom chamber 121" separated from each other by a barrier 104a. In this second embodiment, the bottom chamber includes at least two inter-digitizing inflatable chambers 121a and 121b separated by a second barrier 104b. Compartments 121a and 121b are fed individually with their own regulated compressed air supply through inlets 110a and 110b as shown. Ambient air is delivered into the bottom compartment and the two inter-digitizing inflatable chambers 121a and 121b. These inter-digitizing inflatable chambers serve as an alternating pressure pad and include apertures 121a' and 121b' integrated therein that feed into the bottom chamber and deliver air out of the bottom apertures 108'. P indicates a pressure source and the circle with an arrow indicates a regulator. A filter 107 is integrated within mating attachment means 106' within inlet 3106 so that the air inflow (low flow heated/cooled) to the top chamber 120 is filtered to remove bacteria and contaminants that can cause infection.

In another embodiment, the apertures of the top surface of the top chamber may be confined to the upper/head region of the pad, rather than the entire length of the pad. Alternatively, the apertures may instead be confined to the lower portion/lower leg and foot region of the pad.

The key features of the patient lifter system wherein intraoperative controlled temperature air surrounds a patient comprise, in combination:

i) a pad with a top chamber and a bottom chamber separated by a barrier;

ii) said top chamber being provided with a plurality of small apertures on its top surface;

iii) said top chamber having an inlet with a filter integrated therein so that the air inflow (low flow heated/cooled) to the top chamber is filtered to remove bacteria and contaminants, thereby delivering clean air without bacteria through the top chamber which is released around the patient, minimizing infection risk;

iv) said top chamber being provided with a low pressure supply of compressed heated air or cooled air;

v) heated or cooled air being delivered from below the patient to surround the patient;

vi) a surgical drape surrounding the patient to provide comfort to the patient without need for a tent or other hardware;

vii) said bottom chamber being provided with a supply of compressed ambient air at a pre-selectable regulated air pressure;

viii) said bottom chamber having a plurality of apertures on its bottom surface;

ix) said ambient air pressure inflating said bottom chamber and being portative to supporting a patient lying on the top surface of the top chamber and the ambient pressure of the bottom surface having a pre-selected low value, minimally discharging ambient air;

x) during lateral movement of the patient lying on said pad, the compressed ambient air pressure being increased to a pre-selected high pressure, discharging air through said bottom surface of said bottom chamber to thereby create an air cushion directly under the pad with the patient, allowing easy effort-free movement of the patient from a stretcher to an operating table or from a bed to a stretcher; and xi) the subject pad is the only patient heater that supports the patient's head during lateral transfer and avoids neck strains without requiring the anesthetist to hold the patient's head while the patient is being moved.

In a second embodiment, the pad having a bottom chamber comprising two laterally separated inter-digitizing inflatable chambers therein, each being provided with an individually regulated compressed ambient air supply, for adjusting pressure points.

Advantageously, the Patient Lifter with Intraoperative Heater System provides:

i) a combination system with operative heater that delivers clean filtered warm or cold air stream surrounding a patient and a patient lifter/patient transport device, wherein the air travels through a filter removing bacteria and contaminants and mitigating risk of infection to the patient;

ii) an intraoperative heater device that delivers heat from beneath a patient, and which can be used without a tent, the system having surgical drapes that are placed above the patient and function as a cover when heat is delivered from beneath the patient;

iii) an air-cushion forming mechanism for developing compressed ambient air pressure that is increased to a pre-selected high pressure, discharging air through said bottom surface of said bottom chamber to thereby create an air cushion that facilitates lateral movement of the patient onto an operating table or a hospital bed;

iv) an intraoperative device that can be used for heating and/or cooling, by providing for the circulation of hot or cool air through a low pressure blower; and v) a patient heater—lateral transfer pad that supports the patient's head during lateral transfer and avoids neck strains without requiring the anesthetist to hold the patient's head while the patient is being moved.

Having thus described the invention in rather full detail, it will be understood that such detail need not be strictly adhered to, but that additional changes and modifications may suggest themselves to one skilled in the art. The bottom section of the patient lifter can be divided into two inter-digitizing compartments that are pulsed from small pressure to a slightly larger pressure with a preselected pulse frequency, while the top chamber is maintained at a small pressure. With this arrangement, the patient lifter functions as an alternating pressure pad, redistributing points of contact pressure extant between the top surface of the pad and body portions of a patient resting thereon to thereby avoid pressure sores and decubiti. The length and width of the pad can be adjusted to produce a half-size pad configuration that still facilitates lateral movement of the upper torso of the patient. Such modifications are considered to fall within the scope of the invention as defined by the subjoined claims. The top chamber filter is preferably integrated within the inlet. However, in an alternative embodiment, the filter may be formed or integrated within the apertures of the top chamber. In this manner, a filtration sheet is preferably bonded behind the apertures of the top chamber so that air is filtered directly and immediately before contacting the patient.

What is claimed is:

1. A patient lifter with an intraoperative controlled temperature air delivery system, comprising:
   a. an air-inflated pad having a top chamber and a bottom chamber separated by a diaphragm formed of a thin flexible non-porous substantially non-rigid material;
   b. said top chamber comprising a top surface having a plurality of air venting apertures therein;
   c. said top chamber having an inlet appointed to be supplied with a regulated controlled low pressure and controlled temperature heated or cooled air;
   d. said bottom chamber comprising a bottom surface having a plurality of air venting apertures therein;
   e. said bottom chamber having an inlet appointed to be supplied with ambient air at a regulated controlled pressure to facilitate lifting and lateral displacement during patient transfer;
   f. said inlet of said top chamber comprising a filter adapted to filter said regulated, controlled low pressure and controlled temperature heated or cooled air to remove bacteria and deliver clean filtered heated or cooled air from said air venting apertures of said top chamber, thereby providing clean filtered air around a patient;
   g. said top chamber being a single chamber free from springs or barriers therein;
   h. said top surface being substantially a planar flat surface terminating at end walls, said end walls extending downward from said top surface of said top chamber toward said bottom chamber, and said plurality of air venting apertures being flush mounted in said top surface so that said apertures do not protrude from said top surface;
   i. said bottom chamber being substantially flat and said plurality of air venting apertures creating a cushion of air below said lifter to enable transfer of said patient; and
   j. said inlet of said top chamber comprising an attachment piece, said attachment piece having a channel engageable with a tooth of a complimentary fitting, said filter being located on the inside surface of said attachment piece and said inlet of said top chamber;
   whereby heated air or cooled air is discharged from said top surface, and formation of an air cushion from said bottom surface facilitates lateral translation on a flat or irregular surface and reduces stress on both patient and hospital personnel.

2. A patient lifter with an intraoperative controlled temperature air delivery system as recited by claim 1 comprising a single blower with variable air output and a heater that can be switched on or off, wherein high pressure air flow without heat is appointed to be delivered to the bottom chamber for transfer function and low pressure with heated or cooled air in the upper chamber being appointed for delivery to maintain correct patient temperature.

3. A patient lifter with an intraoperative controlled temperature air delivery system as recited by claim 1, wherein the bottom chamber is divided into at least two interdigitizing compartments that are pulsed to deliver alternating pressure.

4. A patient lifter with an intraoperative controlled temperature air delivery system as recited by claim 1, including a surgical drape.

5. A patient lifter with an intraoperative controlled temperature air delivery system as recited by claim 1, wherein said air inflated pad is disposed on a stretcher and, during lateral displacement of a patient on said air-inflated pad from said stretcher to an operating table, a high bottom chamber pressure is maintained, creating an air cushion under the bottom surface of said air-inflated pad that facilitates lateral movement of said air inflated pad and the patient.

6. A patient lifter with an intraoperative controlled temperature air delivery system as recited by claim 1, wherein said air inflated pad is disposed on a stretcher and, during lateral displacement of a patient on said air-inflated pad from said stretcher to a hospital bed, a high bottom chamber pressure is maintained, creating an air cushion under the bottom surface of said air-inflated pad that facilitates lateral movement of said air inflated pad and the patient.

7. A patient lifter with an intraoperative controlled temperature air delivery system as recited by claim 1, wherein said bottom chamber has a thickness ranging between ½ and 3 inches.

8. A patient lifter with an intraoperative controlled temperature air delivery system as recited by claim 1, wherein said bottom chamber comprises a substantially unilateral chamber free from springs or other protrusions.

9. A patient lifter with an intraoperative controlled temperature air delivery system as recited by claim 1, wherein said the bottom chamber comprises a plurality of sections arranged in an interlocking "S" or comb-shaped configuration.

10. A patient lifter with an intraoperative controlled temperature air delivery system as recited by claim 1, wherein said air-inflated pad is fabricated from a thin, flexible disposable material for single use.

11. A patient lifter with an intraoperative controlled temperature air delivery system, comprising:
   a. an air-inflated pad having a top chamber and a bottom chamber separated by a diaphragm formed of a thin flexible non-porous substantially non-rigid material;
   b. said top chamber comprising a top surface having a plurality of air venting apertures therein;
   c. said top chamber being a single chamber free from springs or barriers therein and having an inlet appointed to be supplied with a regulated controlled low pressure and controlled temperature heated or cooled air;
   d. said inlet of said top chamber having a filter adapted to filter said regulated, controlled pressure and controlled temperature heated or cooled air to remove bacteria and deliver clean filtered heated or cooled air from said air venting apertures of said top chamber and provide clean filtered air around a patient;
   e. said plurality of air venting apertures of said top surface of said top chamber leaking heated or cooled air when said regulated controlled pressure is low, causing said heated or cooled air to surround a patient;
   f. said bottom chamber comprising a bottom surface having a plurality of air venting apertures therein;
   g. said bottom chamber having an inlet appointed to be supplied with ambient air at a regulated controlled pressure to facilitate lifting and lateral displacement during patient transfer;
   h. said top chamber being a single chamber free from springs or barriers therein;
   i. said top surface being substantially a planar flat surface terminating at end walls, said end walls extending downward from said top surface of said top chamber toward said bottom chamber, and said plurality of air venting apertures being flush mounted in said top surface so that said apertures do not protrude from said top surface;
   j. said bottom chamber being substantially flat and said plurality of air venting apertures creating a cushion of air below said lifter to enable transfer of said patient; and
   k. said inlet of said top chamber comprising an attachment piece, said attachment piece having a channel engageable with a tooth of a complimentary fitting, said filter being located on the inside surface of said attachment piece and said inlet of said top chamber;
   whereby heated air or cooled air is appointed to be provided to enhance patient comfort, reducing stress on both patient and hospital personnel, and requiring fewer hospital personnel to achieve safe transport of the patient from one surface to another.

12. A patient lifter with an intraoperative controlled temperature air delivery system as recited by claim 11, wherein said bottom chamber has a substantially flat bottom surface.

\* \* \* \* \*